United States Patent [19]

Hilboll et al.

[11] Patent Number: 4,551,455

[45] Date of Patent: Nov. 5, 1985

[54] METHOD OF TREATING HIGH BLOOD PRESSURE USING 6-[4-(1-IMIDAZOLYL)-PHENYL]-5-METHYL-3-OXO-TETRAHYDROPYRIDAZINES

[75] Inventors: Gerd Hilboll, Cologne; Ille-Stephanie Doppelfeld, Bergheim-Giessen; Gerrit Prop, Pulheim, all of Fed. Rep. of Germany

[73] Assignee: A. Nattermann & Cie GmbH, Cologne, Fed. Rep. of Germany

[21] Appl. No.: 478,993

[22] Filed: Mar. 25, 1983

[30] Foreign Application Priority Data

Apr. 2, 1982 [DE] Fed. Rep. of Germany ....... 3212304

[51] Int. Cl.$^4$ .................. C07D 237/06; A61K 31/50
[52] U.S. Cl. ...................................... 514/252; 544/238
[58] Field of Search ............... 544/238; 424/250; 514/252

[56] References Cited

U.S. PATENT DOCUMENTS

| | | | |
|---|---|---|---|
| 4,088,762 | 5/1978 | Hakim et al. | 544/239 |
| 4,353,905 | 10/1982 | Sircar et al. | 544/239 |
| 4,504,479 | 3/1985 | Lautenschläger et al. | 544/238 |
| 4,507,298 | 3/1985 | Lautenschläger et al. | 544/238 |

FOREIGN PATENT DOCUMENTS

| | | |
|---|---|---|
| 1108614 | 9/1981 | Canada . |
| 0071060 | 7/1981 | European Pat. Off. . |
| 813966 | 6/1981 | South Africa . |

OTHER PUBLICATIONS

L. M. Sitkina and A. M. Simonov, Chem. Abstr., 65, 13686e (1966).
H. Stetter, Angew. Chem., 88, 695–736 (1976).
Born, Nature, 194, pp. 927–929 (1962).

*Primary Examiner*—Nicholas S. Rizzo
*Attorney, Agent, or Firm*—Pearne, Gordon, Sessions, McCoy, Granger & Tilberry

[57] ABSTRACT

The present invention relates to new 6-[Imidazolyl-phenyl]-5-methyl-3-oxo-tetrahydropyridazines of the general formula I

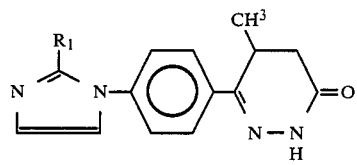

as well as their acid addition salts, methods for their use, and pharmaceutical preparations containing them.

3 Claims, No Drawings

METHOD OF TREATING HIGH BLOOD PRESSURE USING 6-[4-(1-IMIDAZOLYL)-PHENYL]-5-METHYL-3-OXO-TETRAHYDROPYRIDAZINES

The present invention relates to new 6-[4-(1-(imidazolyl)phenyl]-5-methyl-3-oxotetrahydropyridazines and their pharmaceutically compatible acid addition salts, methods for their preparation, pharmaceutical preparations containing these compounds, and their application to the treatment of high blood pressure and the prophylaxis and therapy of thromboembolistic diseases.

The prior art discloses 6-(acylaminophenyl)-3-oxotetrahydropyridazine compounds. For example, in Canadian Pat. No. 1,108,614 these compounds are described substituted on the alkanoyl group with one or more halogen atoms, and they are indicated to have thrombocyte-aggregation-suppressing and blood pressure-lowering properties. Similar properties are specified for the compounds substituted on the phenyl ring by a carbonate group in South African Patent Application No. 81/03966.

It has now been found that 6-(imidazolylphenyl)-5-methyl-3-oxotetrahydropyridazines of formula I,

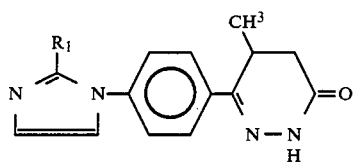

wherein $R_1$ signifies a hydrogen atom or a methyl group, exhibit valuable pharmacological properties. The acid addition salts of compounds of formula I are also included. The acid addition salts are especially applicable pharmaceutically, for example, those with hydrochloric acid, hydrobromic acid, sulfuric acid, or phosphoric acid, or with organic acids such as suitable carboxylic acids, for example, acetic acid, propionic acid, oxalic acid, malonic acid, glycolic acid, succinic acid, maleic acid, fumaric acid, and malic acid.

The compounds of formula I possess a center of chirality at the 5 position of the pyridazine ring, and thus can exist as the racemate or in the form of the separate enantiomers. If a resolution of the racemate is desired, this is accomplished expediently following known methods for this purpose with an optically active acid, as for example dibenzoyltartaric acid or camphor-10-sulfonic acid through the formation of the diastereomeric salts or else by chromatography on an optically active column material.

The compounds pertinent to the invention are: 6-[4-(1-imidazolyl)phenyl]-5-methyl-3-oxo-2,3,4,5-tetrahydropyridazine and 6-[4-(2-methyl-1-imidazolyl)phenyl]-5-methyl-3-oxo-2,3,4,5-tetrahydropyridazine.

The pertinent tetrahydropyridazines of formula I are distinguished by strong blood pressure-lowering and thrombocyte-aggregation-suppressing properties. They are thus suited to the treatment of persons suffering from arteriosclerosis and/or high blood pressure, i.e., as antihypertensives and for the prophylaxis and therapy of thromboembolitic diseases.

The preparation of the substances of formula I pertinent to the invention result from the reaction of 4-(imidazolyl-phenyl)-3-methyl-4-oxobutyric acids of formula II, wherein $R_1$ has the significance given for formula I, with hydrazine or its hydrate or salts such as the hydrochloride, hydrogen sulfate, or sulfate, among others, in aqueous, aqueous alcoholic, or alcoholic media, or in organic solvents inert under the chosen conditions, as for example, dioxane, toluene, or dimethyl foramide, at temperatures of 60°–150° C., preferably at 80°–100° C. in ethanol or water. The reaction is illustrated by the following equation:

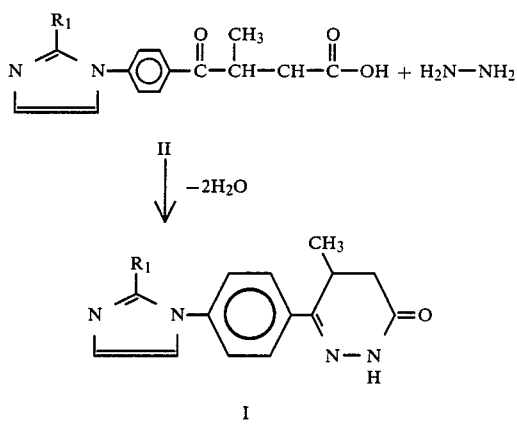

The following starting materials are used to provide the compounds of formula II: 4-[4-(1-imidazolyl)phenyl]-3-methyl-4-oxobutyric acid and 4-[4-(2-methyl-1-imidazolyl)phenyl]-3-methyl-4-oxobutyric acid.

The preparation of the starting compounds of formula II takes place according to known methods: 4-(1-imidazolyl)benzaldehydes of formula III (see L. M. Sitkina and A. M. Simonov, Chem. Abstr., 65, 13686e, (1966)) are reacted under the catalytic influence of sodium cyanide (H. Stetter, Angew. Chem., 88, 695–736 (1976)) with 2-butenenitrile to give the 4-(imidazolylphenyl)-3-methyl-4-oxobutyronitriles of formula IV, which are converted by hydrolysis with hydrochloric acid into the 4-(imidazolylphenyl)-3-methyl-4-oxobutyric acids of formula II. The reaction is illustrated in the following scheme:

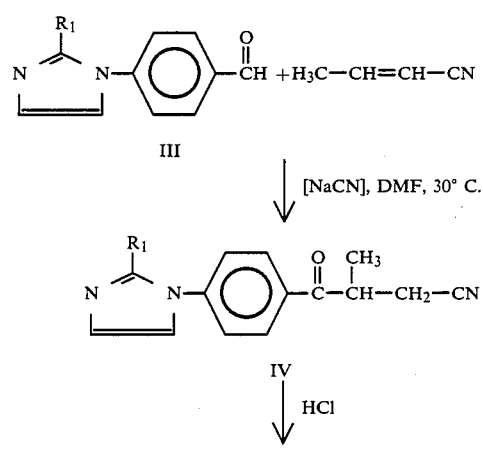

-continued

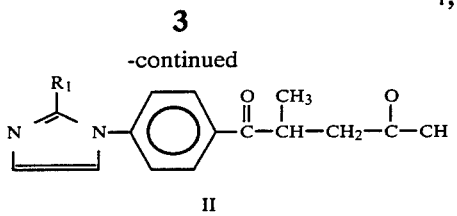

II

The acid addition salts of the compounds of formula I with inorganic or organic acids can be prepared by combination of the imidazolyl compounds on which they are based, with the corresponding acids in aqueous, aqueous organic (for example, alcohol water), or organic media, as for example alcohols, alcohol ether mixtures, or ether petroleum ether mixture at temperatures between 0° and 100° C.

For investigation of the pharmacodynamic properties, the following methods (1) through (4) were employed.

(1) The blood pressure-lowering effect on narcotized rats was evaluated. For testing of the blood pressure-lowering effect, the invention substance 6-[4-(imidazolyl)phenyl]-5-methyl-3-oxo-2,3,4,5-tetrahydropyridazine (A) was administered in parallel with the reference substance 1-hydrazinophthalazine (hydralazine) (C) orally to groups of 5 male adult normotensive Wistar rats. Ninety minutes after application, the animal was narcotized with 75 mg/kg of intraperitoneal phenobarbital, and the trachea and the carotid artery were cannulated. The measured blood pressure and heartbeat frequency values are collected in Table 1.

TABLE 1

| Substance | Dosage mg/kg orally | n* | Average arterial pressure mmHg | Heart frequency beats/min. |
|---|---|---|---|---|
| Control | — | 19 | 112.8 ± 4.8 | 307 ± 11 |
| A | 3.16 | 5 | 54.8 ± 8.9 | 415 ± 17 |
| C | 3.16 | 5 | 82.0 ± 6 | 356 ± 8 |

*n = number of animals (2) The blood pressure-lowering effect on anaesthetized dogs was evaluated. The influence on the systolic and diastolic blood preessure of the subject compounds 6-[4-(1-imidazolyl)phenyl]-5-methyl-3-oxo-2,3,4,5-tetrahydropyridazine (A) and 6-[4-(2-methyl-1-imidazolyl)-phenyl]-5-methyl-3-oxo-2,3,4,5-tetrahydropyridazine (B) were studied on the anaesthetized dogs by intraduodenal administration.

TABLE 2

| Substance | Dosage mg/kg intraduodenally | Pressure, Δ mmHg systolic | diastolic |
|---|---|---|---|
| A | 0.316 | −51.77 | −51.42 |
| B | 0.316 | −48.18 | −43.80 |

(3) The inhibition of collagen-induced thrombocyte aggregation in vitro was evaluated. The suppression of collagen-induced thrombocyte aggregation in vitro was carried out on thrombocyte-rich human plasma with the inventive substance 6-[4-(1-imidazolyl)-phenyl]-5-methyl-3-oxo-2,3,4,5-tetrahydropyridazine (A) in parallel with the reference substance acetylsalicyclic acid (D) according to the method of Born (Nature, 194, 927–929 (1962)) in modified form (simultaneous application). The concentration that caused a 50% reduction of the aggregation was defined as $IC_{50}$ in Table 3 set forth below.

TABLE 3

| Substance | $IC_{50}$ (Mol/L) |
|---|---|
| A | $2.4 \times 10^{-6}$ |
| D | $>3 \times 10^{-4}$ |

(4) The reduction of thrombin formation in narcotized rats was evaluated. The test of the reduction of thrombin formation by the substances of the present invention 6-[4-(1-imidazolyl)phenyl]-5-methyl-3-oxo-2,3,4,5-tetrahydropyridazine (A) and 6-[4-(2-methyl-1-imidazolyl)-phenyl]-5-methyl-3-oxo-2,3,4,5-tetrahydropyridazoline (B) in parallel with the reference substance acetylsalicylic acid (D) was carried out by oral administration to narcotized rats.

TABLE 4

| Substance | Dosage mg/kg orally | Reduction in % |
|---|---|---|
| A | 10 | −52 |
| B | 10 | −48 |
| D | 100 | −45 |

The results from Table 1 show a powerful blood pressure-lowering effect on the rats of substance A of the present invention in comparison with the recognized antihypertonic hydralizine C. In Table 2, the strong influence on blood pressure of substances A and B of the present invention is demonstrated.

In addition to their blood pressure-lowering effect, the substances of the present invention exhibit a strong inhibition of human thrombocyte aggregation induced by collagen in vitro, as well as a diminution of thrombus formation in narcotized rats in comparison with the known aggregation-inhibiting drug acetylsalicylic acid D, as shown by the tests of Tables 3 and 4.

The present invention also concerns pharmaceutical preparations which contain compounds of formula I or pharmaceutically acceptable acid addition salts of these compounds. With respect to the pharmaceutical preparations pertinent to the present invention, we are concerned with those for enteral, oral or rectal, administration as well as parenteral administration which contain the pharmaceutically active agent alone or together with a common, pharmaceutically feasible carrier material. It is advantageous for the pharmaceutical formulation of the active material to be in the form of individual doses which are consistent with the desired application, as for example tablets, dragees, capsules, suppositories, granulates, solutions, emulsions, or suspensions. The dosage of the compound usually lies between 0.1 and 500 mg per dose, preferably between 1 and 150 mg for each dose, and can be administered one or several times, preferably two to three times, daily.

The preparation of the compounds according to the invention is more precisely illustrated by the following examples. The stated melting points are in °C., and were measured with a Büchi 510 melting-point apparatus, and are uncorrected. The IR spectra were recorded on a Perkin Elmer 257 instrument, and the mass spectra were obtained with a Varian-MAT 311-A instrument operating at 70 eV.

EXAMPLE 1

6-[4-(1-Imidazolyl)phenyl]-5-methyl-3-oxo-2,3,4,5-tetrahydropyridazine (a)

4-[4-(Imidazolyl)phenyl]-3-methyl-4-oxo-butyronitrile

To a mixture of 17.2 g of 4-(1-imidazolyl)-benzaldehyde and 250 ml of dimethylformamide under a nitrogen atmosphere was added 0.39 g of sodium cyanide and then with stirring at 30° C. 5.36 g of 2-butenenitrile was added dropwise within 30 minutes. The reaction mixture was stirred at 25° C. under nitrogen for another 24 hours. Following the addition of 500 ml of water, the mixture was extracted with choroform, and the chloroform phase was washed with water, dried over sodium sulfate, and concentrated. The residue was purified by column chromatography (silica gel/chloroform) and then reprecipitated with chloroform/n-hexane.

Yield: 14.5 g (76% of theoretical)
Mp: 109° C.;
IR (in KBr): 2254, 1677 cm$^{-1}$
MS [m/e]: 239 (M+, 62%), 212 (5%), 171 (100%), 143 (65%), 116 (74%).

(b) 4-[4-(1-Imidazolyl)phenyl]-3-methyl-4-oxo-butyric acid

4-[4-(1-Imidazolyl)phenyl]-3-methyl-4-oxobutyronitrile (110 g) was heated under reflux with 860 ml of 25% hydrochloric acid under a nitrogen atmosphere for 2 hours. After cooling, the mixture was brought to pH 9 by the addition of 20% sodium hydroxide solution and extracted with chloroform. The aqueous phase was then adjusted to pH 5.8 by the addition of 10% hydrochloric acid and stirred at 25° C. for 8 hours. The precipitated solid was collected by filtration, washed with water, and dried.

Yield: 92.9 g (78% of theoretical)
Mp: 185° C.;
IR (in KBr): 1705, 1677 cm$^{-1}$
MS [m/e]: 258 (M+, 16%), 240 (4%), 171 (100%), 143 (15%), 116 (15%).

(c)

6-[4-(1-Imidazolyl)phenyl]-5-methyl-3-oxo-2,3,4,5-tetrahydropyridazine

4-[4-(1-Imidazolyl)phenyl]-3-methyl-4-oxobutyric acid (75.7 g) was suspended in 145 m of water. After the addition of 17 ml of hydrazine hydrate, the reaction mixture was stirred at reflux temperature for 2 hours. After cooling, the precipitated solid was collected by filtration, washed with water, and dried.

Yield: 64.6 g (87% of theoretical)
Mp: 199° C.
IR (in KBr): 1687, 1613 cm$^{-1}$
MS [m/e]: 254 (M+, 100%), 239 (13%), 211 (3%), 197 (10%), 183 (7%), 169 (11%), 142 (8%), 115 (10%), 102 (4%)

EXAMPLE 2

6-[4-(2-Methyl-1-imidazolyl)phenyl]-5-methyl-3-oxo-2,3,4,5-tetrahydropyridazine (a)

4-[4-(2-Methyl-1-imidazolyl)phenyl]-3-methyl-4-oxobutyronitrile

To a mixture of 33.6 g of 4-(2-methyl-1-imidazolyl)-benzaldehyde and 400 ml of dimethylformamide under a nitrogen atmosphere was added 0.78 g of sodium cyanide and then with stirring at 30° C. 10.7 g of 2-butenenitrile was added dropwise. The reaction mixture was stirred at 25° C. under nitrogen for another 16 hours. Following the addition of one liter of water the mixture was extracted with chloroform, and the chloroform phase was washed with water, dried over sodium sulfate, and concentrated. The residue was purified by column chromatography (silica gel/chloroform) and then reprecipitated with chloroform/hexane.

Yield: 30.5 g (75% of theoretical)
Mp 97°–98° C.
IR (in KBr): 2242, 1680 cm$^{-1}$
MS [m/e]: 253 (M+, 42%), 185 (100%), 157 (27%), 116 (18%).

(b)

4-[4-(2-Methyl-1-imidazolyl)phenyl]-3-methyl-4-oxobutyric acid

4-[4-(2-Methyl-1-imidazolyl)-phenyl]-3-methyl-4-oxobutyronitrile (34.2 g) was heated under reflux in a nitrogen atmosphere for 3 hours with 220 ml of 18% hydrochloric acid. After cooling, the mixture was brought to pH 9 by the addition of 20% sodium hydroxide solution and extracted with chloroform. The aqueous phase was then adjusted to pH 5.8 by the addition of 10% hydrochloric acid and stirred at 25° C. for 8 hours. The precipitated solid was collected by filtration, washed with water, and dried.

Yield: 32.2 g (91% of theoretical)
Mp 172°–173° C.
IR (in KBr): 1705, 1680 cm$^{-1}$
MS [m/e]: 272 (M+, 20%), 254 (24%), 226 (4%), 185 (100%), 157 (30%), 116 (21%).

(c)

6-[4-(2-(Methyl-1-imidazolyl)phenyl]-5-methyl-3-oxo-2,3,4,5-tetrahydropyridazine 4-[4-(2-Methyl-1-imidazolyl)phenyl]-3-methyl-4-oxobutyronitrile (32.2 g) was suspended in 100 ml of water. After the addition of 6.2 ml of hydrazine hydrate, the reaction mixture was stirred at reflux temperature for 2 hours. After cooling, the precipitated solid was collected by filtration, washed with water, and dried.

Yield: 30 g (95% of theoretical)
Mp: 197°–199° C.
IR (in KBr): 1686, 1612 cm$^{-1}$
MS [m/e]: 268 (M+, 100%), 253 (7%), 241 (10%), 183 (15%), 115 (16%).

EXAMPLE 3

6-[4-(1-Imidazolyl)-phenyl]-5-methyl-3-oxo-2,3,4,5-tetrahydropyridazine fumarate A mixture of 5 g of 6-[4-(1-imidazolyl)-phenyl]-5-methyl-3-oxo-2,3,4,5-tetrahydropyridazine and 2.3 g of fumaric acid was heated in 250 ml of ethanol until the solid had all dissolved. The solution was then evaporated to dryness, and the residue was dried.

Yield: 6.8 g
Decomposition point: 213°–214° C.
IR (in KBr): 1704, 1646, 1610 cm$^{-1}$.

EXAMPLE 4

6-[4-(2-Methyl-1-imidazolyl)phenyl]-5-methyl-3-oxo-2,3,4,5-tetrahydropyridazine fumarate A mixture of 2 g of 6-[4-(2-methyl-1-imidazolyl)-phenyl]-5-methyl-3-oxo-2,3,4,5-tetrahydropyridazine and 0.865 g of fumaric acid was heated in ethanol until all the solid had dissolved. The solution was then evaporated to dryness, and the residue was dried.

Yield: 2.7 g

Decomposition point: 185°–190° C.

IR (in KBr): 1682, 1645, 1609 cm$^{-1}$. Examples analogous to 3 and 4 can be prepared, for example, oxalates, succinates, and malonates, as well as inorganic salts such as hydrochlorides and hydrogen sulfates.

EXAMPLE 5

| Example of the formulation: | |
|---|---|
| Active ingredient | 10 mg |
| Polyvinylpyrrolidone (average molecular weight 25000) | 170 mg |
| Polyethylene glycol (average molecular weight 4000) | 14 mg |
| Hydroxypropylmethylcellulose | 40 mg |
| Talcum | 4 mg |
| Magnesium stearate | 2 mg |
| | 240 mg |

The active ingredient was moistened with polyvinylpyrrolidone in 10% aqueous solution, forced through a sieve of 1.0-mm open-mesh width, and dried at 50° C. This granulate was mixed with the polyethylene glycol, hydroxypropylmethylcellulose, talcum, and magnesium stearate and pressed into 240-mg tablets.

What is claimed is:

1. A method for the treatment of humans suffering from high blood pressure comprising administering a compound of general formula I,

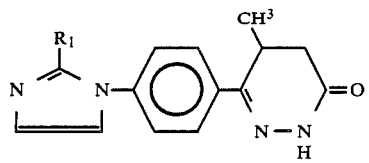

wherein $R_1$ is a hydrogen atom or a methyl group, and their pharmaceutically compatible acid-addition salts with inorganic or organic acids, in a dosage between 0.1 and 500 mg one to three times daily.

2. A method for the treatment of humans suffering from high blood pressure comprising administering 6-[4-(1-imidazolyl)phenyl]-5-methyl-3-oxo-2,3,4,5-tetrahydropyridazine or its pharmaceutically compatible salts in a dosage between 0.1 and 500 mg one to three times daily.

3. A method for the treatment of persons suffering from high blood pressure comprising administering 6-[4-(2-methyl-1-imidazolyl)phenyl]-5-methyl-3-oxo-2,3,4,5-tetrahydropyradazine or its pharmaceutically compatible salts in a dosage between 0.1 and 500 mg one to three times daily.

* * * * *